US008974658B2

(12) United States Patent
Newman et al.

(10) Patent No.: US 8,974,658 B2
(45) Date of Patent: Mar. 10, 2015

(54) ELECTROCHEMICAL DETECTION OF MAGNETIC PARTICLE MOBILITY

(75) Inventors: Peter Michael Newman, Ashburton (AU); Ronald Christopher Chatelier, Bayswater (AU)

(73) Assignee: Universal Biosensors Pty Ltd, Rowville (AU)

( * ) Notice: Subject to any disclaimer, the term of this patent is extended or adjusted under 35 U.S.C. 154(b) by 648 days.

(21) Appl. No.: 12/374,276

(22) PCT Filed: Jul. 13, 2007

(86) PCT No.: PCT/IB2007/001990
§ 371 (c)(1),
(2), (4) Date: Jan. 16, 2009

(87) PCT Pub. No.: WO2008/010058
PCT Pub. Date: Jan. 24, 2008

(65) Prior Publication Data
US 2009/0301901 A1 Dec. 10, 2009

Related U.S. Application Data

(60) Provisional application No. 60/831,240, filed on Jul. 17, 2006.

(51) Int. Cl.
*G01N 27/26* (2006.01)
*G01N 33/50* (2006.01)
(Continued)

(52) U.S. Cl.
CPC .... *G01N 33/4905* (2013.01); *G01N 2011/0086* (2013.01); *G01N 2011/147* (2013.01); *G01N 2015/1075* (2013.01)
USPC ............ 205/792; 205/775; 435/13; 73/54.01; 73/54.02

(58) Field of Classification Search
CPC ... G01N 33/4905; G01N 33/49; G01N 33/50; G01N 27/327–27/3278
USPC .......... 205/792, 775; 204/411, 412, 545, 554, 204/557, 403.01–403.15; 422/73; 73/54.01, 73/54.02; 435/13
See application file for complete search history.

(56) References Cited

U.S. PATENT DOCUMENTS

| 4,849,340 A | 7/1989 | Oberhardt |
| 5,658,723 A | 8/1997 | Oberhardt |

(Continued)

FOREIGN PATENT DOCUMENTS

| DE | 3522098 C2 | 1/1987 |
| EP | 0 467 759 B1 | 1/1992 |

(Continued)

OTHER PUBLICATIONS

Examination Report in related New Zealand Patent Application No. 574714, dated Oct. 6, 2011, 2 pages.
(Continued)

*Primary Examiner* — Luan Van
*Assistant Examiner* — Maris R Kessel
(74) *Attorney, Agent, or Firm* — Davis Wright Tremaine LLP

(57) ABSTRACT

An exemplary embodiment of the invention may include a method for electrochemically monitoring the mobility of particles in a fluid in response to an external field, the method may include monitoring an electrical characteristic of the fluid in an electrochemical cell, the fluid comprising particles that can be moved under the influence of an externally applied field; observing changes in the electrical characteristic caused by particle movement induced by the external field; and inferring a change in the physical state of the fluid from a change in the magnitude of the electrical characteristic observed.

18 Claims, 6 Drawing Sheets

Graph of an exemplary coagulation reaction

(51) Int. Cl.
*G01F 1/64* (2006.01)
*C12Q 1/56* (2006.01)
*G01N 33/49* (2006.01)
*G01N 11/00* (2006.01)
*G01N 11/14* (2006.01)
*G01N 15/10* (2006.01)

(56) References Cited

U.S. PATENT DOCUMENTS

| | | | |
|---|---|---|---|
| 5,670,329 | A | 9/1997 | Oberhardt |
| 6,060,323 | A | 5/2000 | Jina |
| 6,159,353 | A * | 12/2000 | West et al. .................. 204/603 |
| 6,610,186 | B1 * | 8/2003 | Mayer et al. ................. 204/451 |
| 6,620,310 | B1 * | 9/2003 | Ohara et al. .................. 205/792 |
| 7,144,495 | B2 | 12/2006 | Teodorczyk et al. |
| 2003/0077649 | A1 | 4/2003 | Cho et al. |
| 2004/0011672 | A1 | 1/2004 | Ohara et al. |
| 2004/0072357 | A1 | 4/2004 | Stiene et al. |
| 2004/0166552 | A1 * | 8/2004 | Zheng et al. .................. 435/13 |

FOREIGN PATENT DOCUMENTS

| | | |
|---|---|---|
| EP | 1 391 716 A2 | 2/2004 |
| EP | 1 482 296 B1 | 12/2004 |
| JP | H07-311136 | 11/1995 |
| TW | 200413718 | 8/2004 |
| WO | WO 8910788 | 11/1989 |
| WO | WO 99/05516 A1 | 2/1999 |
| WO | WO-99/44060 A1 | 9/1999 |
| WO | WO 02/48707 | 6/2002 |
| WO | WO 2005114140 | 12/2005 |

OTHER PUBLICATIONS

International Search Report issued Oct. 1, 2007 in International Patent Application No. PCT/IB2007/001990.
Written Opinion issued Oct. 1, 2007 in International Patent Application No. PCT/IB2007/001990.
Office Action for Application No. 0701003567, "Electrochemical Detection of Magnetic Particle Mobility", Chatelier et al., w/English Translation.
European Search Report, mailed in related European Patent Application No. 07766626.1, dated Jun. 7, 2010, 7 pages.
Office Action mailed in related Mexican Patent Application No. MX/a/2009/000544, received on May 30, 2011, 1 page.
Examination Report, mailed in related New Zealand Patent Application No. 574714, dated Jul. 12, 2010, 2 pages.
Australian Patent Office, "Examiner's first report," in corresponding Australian Patent Application No. 2007274779 dated Apr. 23, 2012, 2 pages.
New Zealand Patent Office, "Examination Report," in corresponding New Zealand Patent Application No. 574714 dated May 24, 2012, 2 pages.
Examination Report issued in related European Patent Application No. 07766626.1, mailed on Feb. 28, 2012, 5 pages.
Office Action issued in related Japanese Patent Application No. 2009-520067, mailed Feb. 21, 2012, 9 pages.
Office Action issued in related Israel Patent Application No. 196555, mailed Jun. 25, 2012, 1 page.
Office Action in related Taiwan Patent Application No. 096126052, dated Aug. 26, 2013, 5 pages.
Office Action in related Canadian Patent Application No. 2,659,152, dated Mar. 7, 2013, received Apr. 25, 2013, 5 pages.
First Examination Notice, mailed in related Chinese Patent Application No. 200780028935.9, dated Jun. 5, 2012, 3 pages.
Canadian Intellectual Property Office, "Official Action," in corresponding Canadian Patent Application No. 2,659,152, dated Jan. 16, 2014, 3 pgs.
Israel Patent Office, "Official Action (English translation only)," in corresponding Israeli Patent Application No. 196555, dated Feb. 3, 2014, 2 pgs.
Israel Patent Office, "Official Action (English translation only)," in corresponding Israeli Patent Application No. 196555, dated Jun. 11, 2013, 2 pgs.
Japan Patent Office, "Official Action (English translation only)," in corresponding Japanese Patent Application No. 2009-520067, dated Feb. 19, 2013, 2 pgs.
Korean Intellectual Property Office, "Official Action (English translation only)," in corresponding Korean Patent Application No. 10-2009-7003086, dated Feb. 21, 2014, 2 pgs.
State Intellectual Property Office of the Peoples' Republic of China, "Examination Report (English translation only)," in corresponding Chinese Patent Application No. 200780028935.9, dated Apr. 26, 2013, 1 pg.
State Intellectual Property Office of the Peoples' Republic of China, "Examination Report (English translation only)," in corresponding Chinese Patent Application No. 200780028935.9, dated Mar. 13, 2014, 2 pgs.
Taiwan Intellectual Property Office, "Examination Statement (English translation only)," in corresponding Taiwanese Patent Application No. 096126052, dated Aug. 26, 2013, 5 pgs.
Taiwan Intellectual Property Office, "Phone Examination Statement (English translation only)," in corresponding Taiwanese Patent Application No. 096126052, dated Jan. 21, 2014, 1 pg.

* cited by examiner

Diagram of an exemplary two-electrode amperometry

Diagram of an exemplary single-use sensor

Diagram of an exemplary meter and strip

Graph of an exemplary coagulation reaction

Exemplary calibration of sensors using plasmas with known INR.

ELECTROCHEMICAL DETECTION OF MAGNETIC PARTICLE MOBILITY

CROSS-REFERENCE TO RELATED APPLICATIONS

This application claims priority to U.S. provisional patent application 60/831,240 filed 17 Jul. 2006 and is the national phase under 35 U.S.C. §371 of PCT/IB2007/001990 filed 13 Jul. 2007, the contents of which are incorporated herein by reference in their entirety.

BACKGROUND OF THE INVENTION

1. Field of the Invention

This application is related generally to electrochemical detection.

2. Description of the Related Art

Amperometry is an area of electrochemistry where a potential is applied across electrodes in a solution and the current flowing through the solution is measured. The potential is typically kept low enough to prevent the electrolysis of water or the electrochemical detection of interferents, but high enough to obtain a measurable signal from the species of interest. When the potential is first applied, the current is relatively high due to the high concentration of electrochemical mediators near the surface of the electrodes. Subsequently, the mediators near the electrode are depleted so the current is reduced. Concurrently, the diffusion of mediators from the bulk solution to the electrode replenishes the spent mediators, thus leading to a slowly decaying current.

BRIEF SUMMARY OF THE INVENTION

An electrochemical method of detecting a change in a mobility of magnetic particles is described. The mobility of particles can be monitored by peaks in current within an electrochemical cell. If the mobility of the particles change (e.g., the liquid becomes solid) then the amplitude of the peaks change. An exemplary embodiment of the invention has application in, among other things, measuring blood coagulation time. An exemplary embodiment of the invention may include a method for electrochemically monitoring the mobility of particles in a fluid in response to an external field, the method may include monitoring an electrical characteristic of the fluid in an electrochemical cell, the fluid comprising particles that can be moved under the influence of an externally applied field; observing changes in the electrical characteristic caused by particle movement induced by the external field; and inferring a change in the physical state of the fluid from a change in the magnitude of the electrical characteristic observed.

One exemplary embodiment of the present invention may include a method for electrochemically monitoring the mobility of particles in a fluid in response to an external field, the method including: monitoring an electrical characteristic of the fluid in an electrochemical cell, the fluid comprising particles that can be moved under the influence of an externally applied field; observing changes in the electrical characteristic caused by particle movement induced by the external field; and inferring a change in the physical state of the fluid from a change in the magnitude of the electrical characteristic observed.

One exemplary embodiment of the present invention may include the method for electrochemically monitoring the mobility of particles in a fluid in response to an external field, where the fluid further comprises at least one soluble electroactive species that is capable of being oxidized or reduced at an electrode in the electrochemical cell.

One exemplary embodiment of the present invention may include the method for electrochemically monitoring the mobility of particles in a fluid in response to an external field, where the electrical characteristic being measured is the electrochemical current by amperometry.

One exemplary embodiment of the present invention may include the method for electrochemically monitoring the mobility of particles in a fluid in response to an external field, where the electroactive species are salts of ferricyanide and ferrocyanide.

One exemplary embodiment of the present invention may include the method for electrochemically monitoring the mobility of particles in a fluid in response to an external field, where the particles are magnetic and move in response to a changing external magnetic field.

One exemplary embodiment of the present invention may include the method for electrochemically monitoring the mobility of particles in a fluid in response to an external field, where the fluid is whole blood or plasma and the change in physical state of the blood or plasma is due to coagulation.

One exemplary embodiment of the present invention may include the method for electrochemically monitoring the mobility of particles in a fluid in response to an external field, where the particles are magnetic and move in response to a changing external magnetic field and the electrical characteristic is the electrochemical current, where an algorithm is adapted to identify peaks in the electrochemical current that are caused by magnetic particle movement and determine the clotting time of blood or plasma.

One exemplary embodiment of the present invention may include the method for electrochemically monitoring the mobility of particles in a fluid in response to an external field, where the algorithm defines the clot time based on when the $n^{th}$ percentile of the data around each point falls below a predetermined threshold, where the $n^{th}$ percentile is in the range of 50-b $100^{th}$ percentile.

One exemplary embodiment of the present invention may include the method for electrochemically monitoring the mobility of particles in a fluid in response to an external field, where the $n^{th}$ percentile is around the $80^{th}$ percentile.

One exemplary embodiment of the present invention may include the method for electrochemically monitoring the mobility of particles in a fluid in response to an external field, where the algorithm calculates the height of peaks in current and defines the clot time based on when the peak height falls below a predetermined threshold.

One exemplary embodiment of the present invention may include the method for electrochemically monitoring the mobility of particles in a fluid in response to an external field, where the algorithm makes peaks in current easier to identify by calculating $i_t - i_{t-2} + i_t - i_{t-1} + i_t - i_{t+2} + i_t - i_{t+1}$ or $i_t - i_{t-1} + i_t - i_{t+1}$, where $i_t$ is the current measured at a given point in time and $i_{t-1}$ the current measured one time point earlier; $i_{t-2}$, two time points earlier; $i_{t+1}$, one time point later and $i_{t+2}$, two time points later One exemplary embodiment of the present invention may include the method for electrochemically monitoring the mobility of particles in a fluid in response to an external field, where the algorithm determines if a peak in current occurred within a predetermined time of changing the magnetic field and defines the clot time based on whether such a peak is under a predetermined threshold.

One exemplary embodiment of the present invention may include the method for electrochemically monitoring the mobility of particles in a fluid in response to an external field, where the electrochemical cell comprises a strip comprising two electrodes.

One exemplary embodiment of the present invention may include the method for electrochemically monitoring the mobility of particles in a fluid in response to an external field, where the two electrodes are parallel to each other and are separated by 0.05 to 0.5 mm, preferably 0.075-0.15 mm, and most preferably 0.09-0.13 mm.

One exemplary embodiment of the present invention may include the method for electrochemically monitoring the mobility of particles in a fluid in response to an external field, where the two or more electrodes are coplanar.

One exemplary embodiment of the present invention may include the method for electrochemically monitoring the mobility of particles in a fluid in response to an external field, where the two electrodes are separated by an electrically insulating layer, where the layer has a cavity cut in it to receive the analyte liquid, as well as an entry port to allow the liquid to enter the cavity and an exit port for the displaced air.

One exemplary embodiment of the present invention may include the method for electrochemically monitoring the mobility of particles in a fluid in response to an external field, where the strip also contains one or more clotting factors which replace the deficient clotting factors in the sample.

One exemplary embodiment of the present invention may include the method for electrochemically monitoring the mobility of particles in a fluid in response to an external field, where the device comprising a strip comprising two electrodes, a fluid receiving area, and a meter connection area, wherein said strip is coupled to the meter via said meter connection area.

One exemplary embodiment of the present invention may include the method for electrochemically monitoring the mobility of particles in a fluid in response to an external field, where the device further comprises a meter comprising a connector for electrically coupling to said electrodes at the meter connection area of said strip, and circuitry for monitoring an electrical characteristic of the fluid in contact with said electrodes.

One exemplary embodiment of the present invention may include the method for electrochemically monitoring the mobility of particles in a fluid in response to an external field, where the device comprising a meter comprising a connector electrically coupling to the electrodes at a meter connection area of the strip, and circuitry monitoring an electrical characteristic of the fluid in contact with the electrodes.

One exemplary embodiment of the present invention may include the method for electrochemically monitoring the mobility of particles in a fluid in response to an external field, where the device further comprises a strip comprising the plurality of electrodes, a fluid receiving area and the meter connection area.

Further features and advantages of the invention, as well as the structure and operation of various embodiments of the invention, are described in detail below with reference to the accompanying drawings.

BRIEF DESCRIPTION OF DRAWINGS

The present invention will be discussed in more detail below, using a number of exemplary embodiments, with reference to the attached drawings, in which.

DETAILED DESCRIPTION OF THE INVENTION

Figure 1:
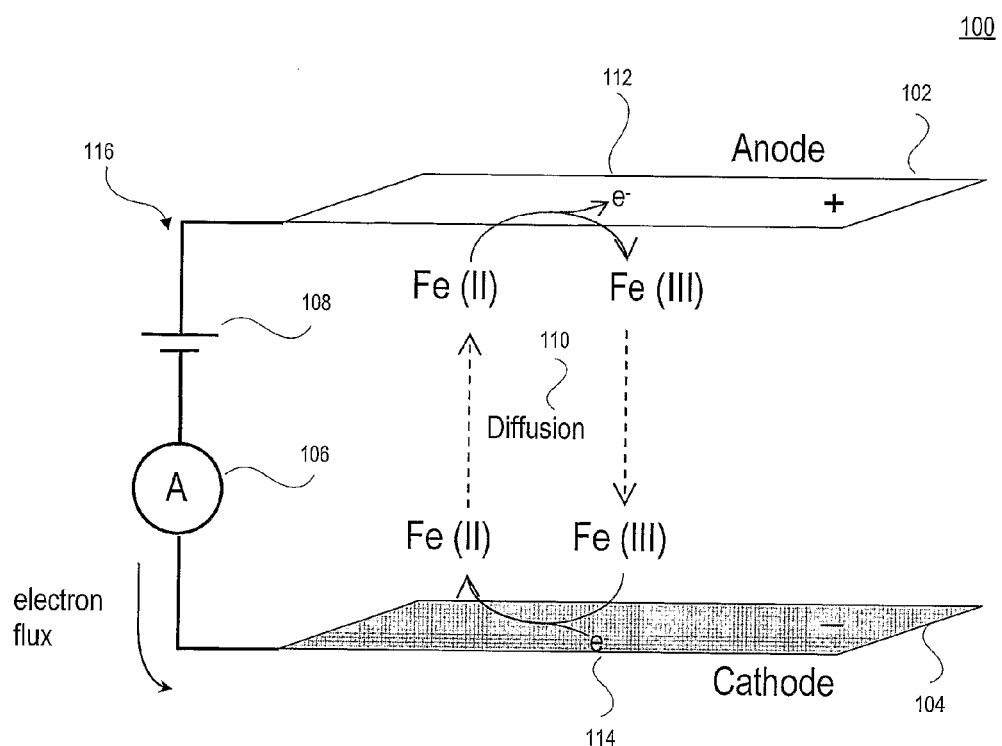
FIG. 1 depicts an exemplary diagram illustrating an exemplary embodiment of a two-electrode amperometry system and process according to an exemplary embodiment.

As illustrated in diagram 100 of FIG. 1 discussed further below, for an electrical current to flow, electrons 112, 114 from an external circuit 116 cause reduction of an electroactive species at the cathode 104 and oxidation of an electroactive species at the anode 102. For a steady state current to be reached, mass transport (diffusion 110, migration or convection) of an electroactive species occurs between the electrodes 102, 104. Importantly, for an exemplary embodiment of the invention, the rate of mass transport can affect the electrical current.

Consider an exemplary embodiment where the electrodes 102, 104 are placed close together and the solution between them contains a blood sample and electrochemical mediators such as ferricyanide ($FE^{III}$) and ferrocyanide ($FE^{II}$). When a small voltage is applied, ferricyanide (containing $Fe^{III}$) is reduced to ferrocyanide (containing $Fe^{II}$), gaining an electron at the negative cathode 104. Similarly, ferrocyanide ($Fe^{II}$) is oxidized to ferricyanide ($Fe^{III}$) by losing an electron to the positive anode 102. This leads to an electrical current in the circuit 116, which can be measured using, e.g., but not limited to an ammeter 106. The reactions taking place at the electrodes 102, 104 can result in a relative accumulation of ferricyanide at the anode 102 and ferrocyanide at the cathode 104. This quickly may result in the electrochemical current falling too close to zero were it not for the fact that the electroactive species can diffuse between the electrodes. Instead, a steady state current is reached where the rate of diffusion of the mediator limits the current. Importantly, anything that causes a mixing of a solution between the electrodes redistributes the electroactive species and produces a transient increase in current, according to an exemplary embodiment.

FIG. 1 depicts an exemplary diagram 100 illustrating an exemplary embodiment of a two-electrode amperometry example using two electrodes 102, 104 and measuring a current using an ammeter 106 through an electrochemical cell 108 as a whole. The reaction at one of the electrodes can limit the current through the whole circuit 116. The limiting electrode is often called the "working" electrode. Other electrochemical cell configurations can be used according to other exemplary embodiments, by introducing more electrodes and more complicated electronics. A three electrode system, for example, can be used to measure the current at a tightly controlled potential at the working electrode. The three electrode embodiment (not shown) can use a "reference" electrode positioned to measure the potential just off the surface of the working electrode. The potential of a "counter" electrode can be constantly adjusted so that the electronic circuit senses the required voltage at the reference electrode, relative to the working electrode. The external circuit measures the current through the working and counter electrodes. Disturbance of the solution around the working electrode can alter the current between the working and counter electrodes. Alternatively, the circuit could be designed to detect changes in the voltage of the counter electrode that is used to maintain a constant current when the solution around the working electrode is disturbed. While a three electrode system may be used in an exemplary embodiment of the present invention, use of three electrodes is not necessary, so examples will be described using an exemplary two electrode system.

The physical state (e.g., solid, liquid or gas, etc.) of a substance is obviously an important characteristic. Changes in a liquid to or from a solid can correspond to important processes such as e.g., freezing/melting, polymerisation, etc. Monitoring such a change can be difficult when sample volumes are small, but an exemplary embodiment of the invention is ideally suited to microliter quantities. In particular, measuring blood plasma coagulation time has an important diagnostic role.

One of the most common coagulation tests is the prothrombin time (PT) test. The PT test is used both for diagnosis and for monitoring warfarin (coumarin) therapy. Warfarin is taken by patients who are at an increased risk of thrombosis (blood clots). The dose of warfarin may be monitored and adjusted so that the patient is neither under nor over anticoagulated. Current guidelines indicate that an International Normalized Ratio (INR) of 2-3 is appropriate in most cases. However, a higher range may be used for some specific indications. The INR system is a method for international standardization of PT tests used to monitor warfarin therapy. The INR system requires that the testing systems be calibrated with standards that are traceable to World Health Organization (WHO) international standards.

Typically coagulation tests are performed on bench-top analysers that can mix patient plasma with a liquid reagent, which is specific for the test, and can time how long the mixture takes to clot. Clotting can be detected by the increased optical turbidity or physically by increased resistance to particle movement through the mixture. Commonly, macroscopic and microscopic magnetic particles are used to monitor coagulation. An oscillating magnetic field can cause the magnetic particles to move, but this movement can cease when the particles become trapped within the clot. Various exemplary ways have been devised for monitoring the particle movement. Conventionally, optical monitoring has been used in a small point-of-care meter. However, optical monitoring may require transparent sensors and can add to the meter cost.

An exemplary embodiment of the invention can use electrochemistry to monitor particle movement. The use of electrochemistry is distinct from monitoring particle movement by some other means (e.g., optical) or from detecting changes in viscosity by changes in electrochemical diffusion coefficient. That is, exemplary embodiments of the invention may repeatedly disturb the limiting mediator concentration at the working electrode, rather than altering the diffusion coefficient of the electroactive species.

Amperometry can be used for clot detection. In the clot detection methods, changes in viscosity are measured by changes in the diffusion coefficient of the electroactive species, in an exemplary embodiment. However, fibrin clots form a relatively loose structure with fully liquid interstitial domains, through which the small electroactive species can move. Therefore, using the clot detection methods, it is often difficult to detect the relatively small changes in the diffusion coefficient of the electroactive species. In contrast, an exemplary embodiment of the invention can use particles that are effectively trapped by the fibrin clot and so are more sensitive to the clotting process.

One exemplary embodiment includes monitoring of liquid gel points. When a liquid gels, the liquid can resist the movement of particles and can decrease peaks in electrochemical current caused by the particle movement. Monitoring liquid gel points could be applied to the coagulation of blood, plasma and other fluids, etc. Similar applications can be found in the assay of gel forming enzymes in food industry.

Another exemplary embodiment can detect the tethering of magnetic particles to a surface that can impede particle mobility. For example, in an exemplary embodiment, beads coated with a specific molecule could become immobilized when the molecule binds a corresponding antibody, antigen, receptor, etc.

Various Exemplary Embodiments of Exemplary Embodiments of Applications

An exemplary embodiment of the invention can be used to construct a device that can measure blood coagulation time using a small sample volume. Such a device can be suited to point-of-care and/or home monitoring of warfarin therapy. The coagulation point of a sample is detected by the loss of movement of particles through the reaction mixture. Typically the particles are magnetic or paramagnetic and are moved by a magnetic field. The movement of the particles can cause a rise in the electrochemical current through the reaction mixture by transiently increasing the concentration of the current-limiting electroactive species at the current-limiting electrode (working electrode). When the reaction mixture coagulates, the particles are unable to move, and the transient rises in current no longer occur. The transition point when particle movement ceases, can be defined as the clot time.

Figure 2:
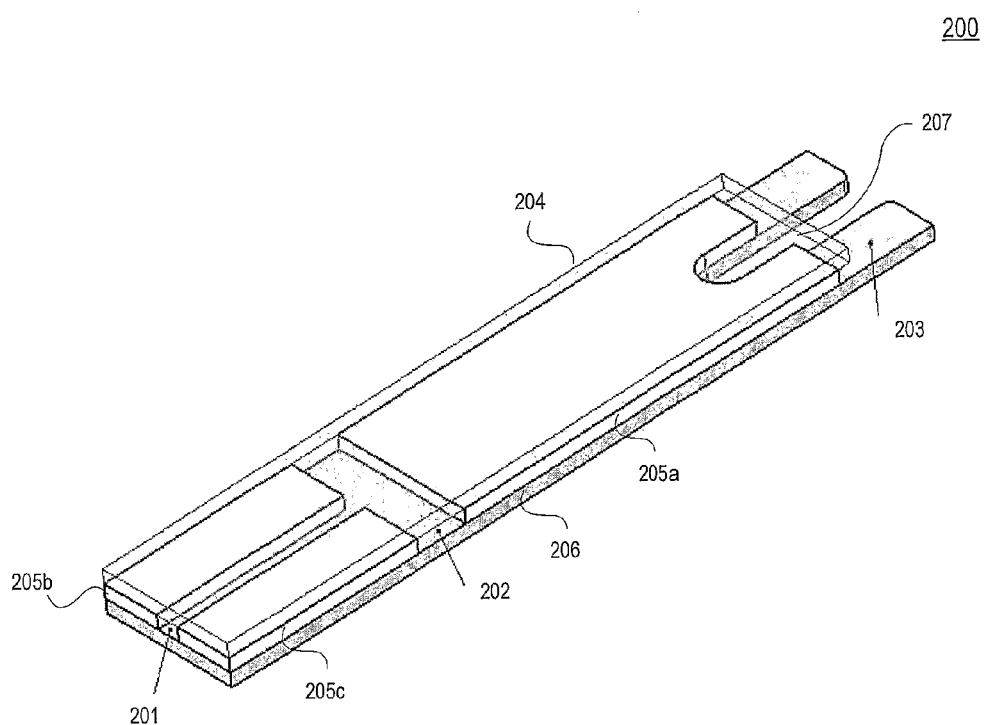
FIG. 2 depicts an exemplary diagram of an exemplary single-use sensor, according to an exemplary embodiment.

In particular exemplary embodiments, an exemplary sensor may include, in an exemplary embodiment, two electrode plates which can face each other, e.g., but not limited to, about 0.1 mm apart. FIG. 2 depicts an exemplary single use sensor 200. An electrically non-conductive separator 205 can keep the electrode plate surfaces 204, 206 parallel and can define the spacing. The shape of the separator and the electrodes can define two chambers that may contain a sample: a fill channel 201 and a detection chamber 202 (see FIG. 2). The fill channel 201 can carry a sample into the detection chamber 202, which can contain dry reagents which may be required to initiate and detect coagulation. Specifically, an exemplary embodiment can contain a coagulation reagent (e.g., but not limited to, thromboplastin, snake venom, contact activators, etc.), magnetic particles and an electrochemical redox couple (e.g., but not limited to, ferricyanide/ferrocyanide, etc.).

Prior to use, the sensor 200 strip 304 can be inserted into the meter 300 described below. Insertion can establish electrical contact by exemplary connectors 203 and can place the detection chamber 202 within the meter housing 302 so that the meter 300 can control the temperature and the magnetic field (see FIG. 3). When the sample (e.g., blood or plasma) is added to the sensor it can travel into the reaction detection chamber 202 via the fill channel 201 and can solubilise the thromboplastin and electrochemical mediators. The meter 300, in an exemplary embodiment, can vary the magnetic field, e.g., using input controls 308, 310, so that the magnetic particles move within the chamber. This can create peaks in the electrochemical current, but the peaks can diminish and may largely disappear when the sample clots and the magnetic particles become immobilized.

The meter 300 can calculate the clot time based on the changes in current and may use calibration information to report the result as an International Normalised Ratio (INR)

312 on, e.g., but not limited to, an exemplary display 306, or other output device. The meter, according to an exemplary embodiment, may also perform error checks and may store the results on e.g., but not limited to, a storage device. An exemplary meter 300 can, e.g., but not limited to, regulate temperature, magnetic field, and/or voltage, and/or can measure electrochemical current.

FIG. 2 depicts an exemplary diagram of an exemplary embodiment of a single-use sensor, according to an exemplary embodiment. A sample may enter the exemplary fill channel 201 and then may move into the exemplary detection chamber 202 by capillary action. The meter may make electrical contact with the meter through connectors 203 and 207 on the end, according to an exemplary embodiment. According to an exemplary embodiment, the top electrode connector 207 may be on the underside of the top electrode plate surface 204, the plate surface covering the slot in the separator 205.

Figure 3:
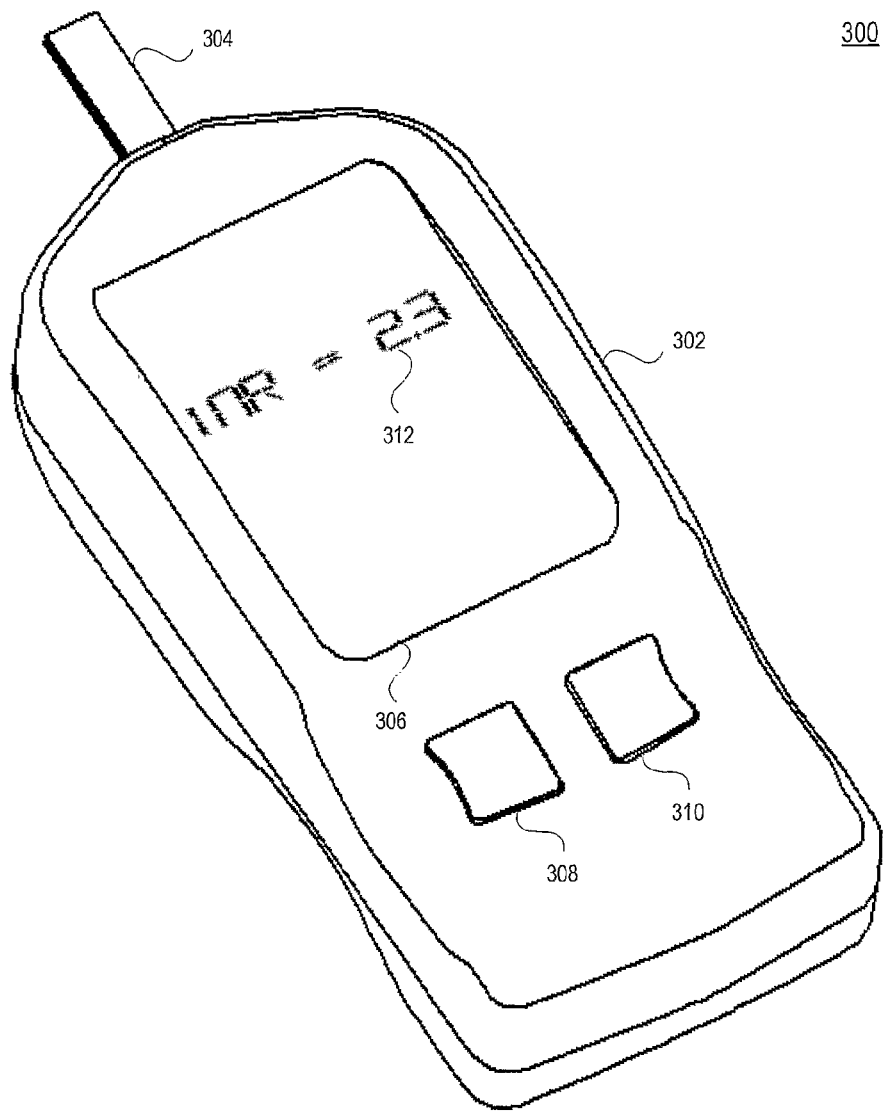
FIG. 3 depicts an exemplary diagram of an exemplary meter and strip, according to an exemplary embodiment.

FIG. 3 depicts an exemplary diagram of an exemplary meter 300 and strip 301, according to an exemplary embodiment. The strip 301 may be inserted into the meter 300 prior to use. The meter 300, according to an exemplary embodiment, can regulate temperature, magnetic field and voltage, etc., and may measure the resulting electrochemical current. An INR, which may be derived from the change in current, may be displayed. The meter 300, in an exemplary embodiment, can detect peaks in electrochemical current and can determine when the current peaks have reduced sufficient exemplary embodiments for a clot point 406 to be defined. There are many ways that this can be done, including, several exemplary embodiments discussed below.

In one exemplary embodiment, the meter may calculate a local maximum that may span at least two peaks. When the local maximum falls below a pre-determined threshold then the clot 406 can be said to have occurred. This method can be refined by using, e.g., but not limited to the local $80^{th}$ percentile, or other predetermined threshold instead of the maximum, in an exemplary embodiment. This method, according to an exemplary embodiment, can make the algorithm more resistant to outliers.

Figure 4:
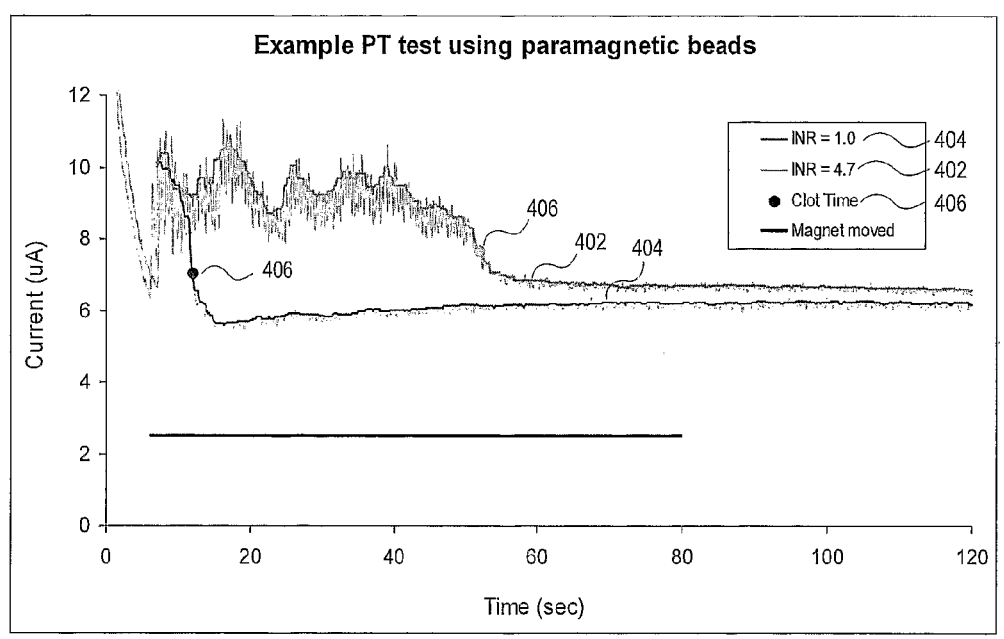
FIG. 4 depicts an exemplary graph of an exemplary coagulation reaction of an exemplary prothrombin time (PT) test using paramagnetic beads, graphing current vs. time, according to an exemplary embodiment.

This approach was used in the exemplary embodiment of the coagulation reaction tested and illustrated in FIG. 4, where an exemplary PT test using para-magnetic beads was performed and current observed as a magnet was moved over time. FIG. 4 depicts an example of a coagulation reaction, according to an exemplary embodiment. An exemplary sensor may contain dry preparations of thromboplastin, para-magnetic beads, ferricyanide and ferrocyanide. In an exemplary embodiment Citrated plasma with known INR (INR Calibration plasmas from Life Therapeutics, Australia) were mixed with 8.5 mM CaCl2 then immediately loaded into sensors. From 6-80 sec a magnet was moved above and below the sensor to move the paramagnetic beads. The fine, light shaded, lines represent the raw currents while the heavier lines show the local 80th percentile around those data. This experiment was conducted with a prototype sensor and meter in a glove-box regulated at 37° C. according to an exemplary embodiment.

Figure 5:
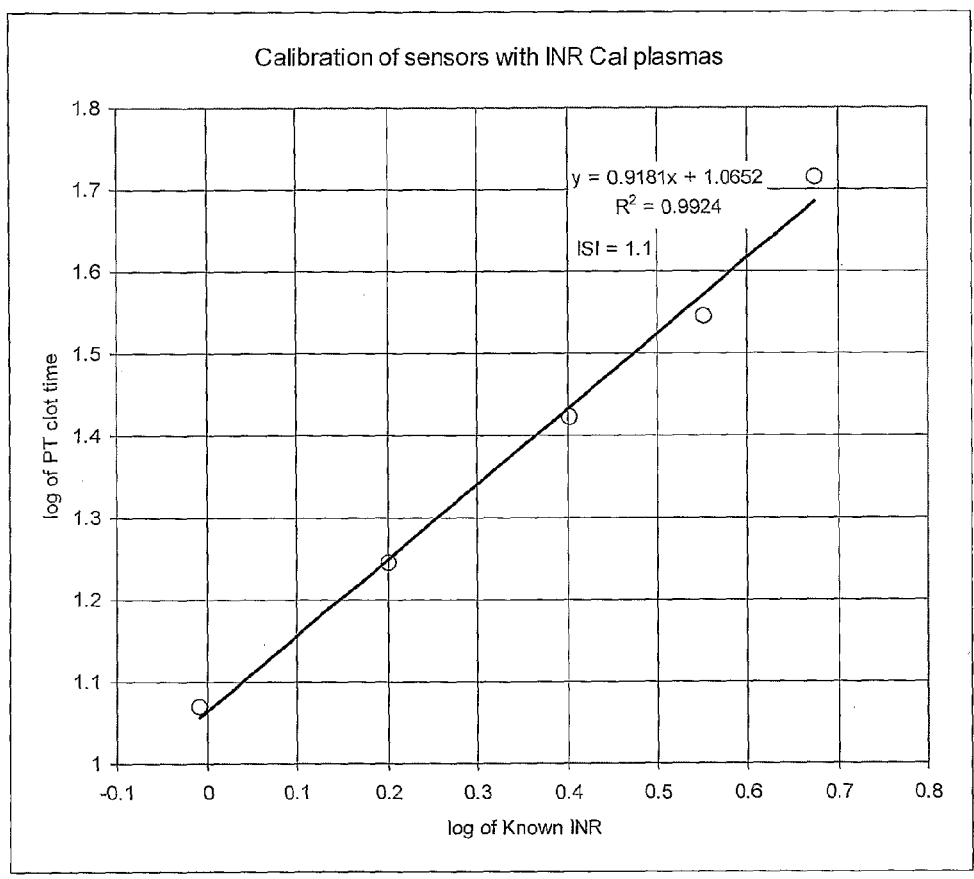
FIG. 5 depicts an exemplary logarithmic graph of an exemplary calibration of sensors using plasmas with known international normalized ratio (INR), graphing PT clot time against known INR, according to an exemplary embodiment.

In another exemplary embodiment, sensors may be calibrated as illustrated in FIG. 5 by using sensors using plasmas of known INR. FIG. 5—depicts an exemplary calibration of sensors using plasmas with known INK according to an exemplary embodiment. In one exemplary embodiment, INR Calibration plasmas (Life Therapeutics, Australia), with assigned INR values, were tested in triplicate with 8.5 mM $CaCl_2$ in the sensors. Plotting log PT against log INR should give a straight line because, by definition, INR=(MNPT/PT) ISI. The straight line will have a slope=1/ISI and a Y-intercept=10 MNPT. An ISI close to 1, and not say 2, is highly desirable. This experiment was conducted with a prototype sensor and meter in a glove-box regulated at 37° C.

Figure 6:
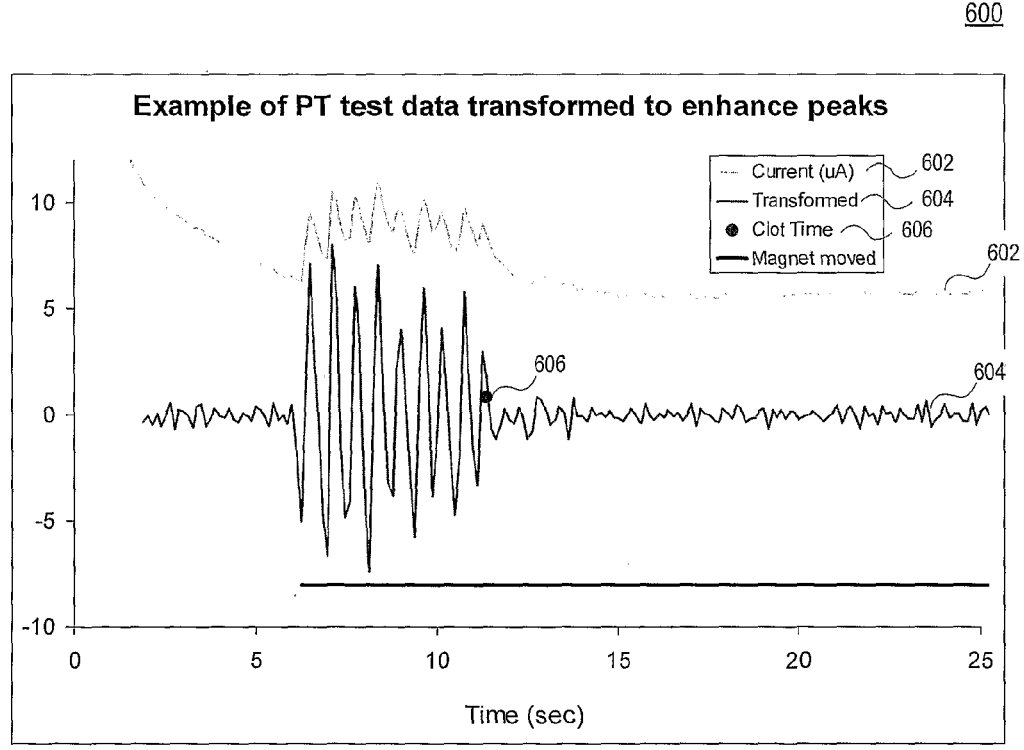
FIG. 6 depicts an exemplary graph of exemplary PT test data transformed to enhance peaks, graphing current vs. time according to an exemplary embodiment.

In another exemplary embodiment, the meter may transform the data to more easily detect peaks and when they cease. For example, the data can be transformed with the function $i_t - i_{t-2} + i_t - i_{t-1} + i_t - i_{t+2} + i_t - i_{t+1}$ or $i_t - i_{t-1} + i_t - i_{t+1}$. Where $i_t$ is the current measured at a given point in time and $i_{t-1}$ the current measured one time point earlier; $i_{t-2}$, two time points earlier; $i_{t+1}$, one time point later and $i_{t+2}$, two time points later. This transformation may enhance the peaks and correct for baseline tilt. This approach is illustrated in FIG. 6, in one exemplary embodiment. FIG. 6 depicts an exemplary test data transformed to enhance peaks, according to an exemplary embodiment. The raw data from INR=1.0 plasma in FIG. 4 are transformed by plotting $i_t - i_{t-2} + i_t - i_{t-1} + i_t - i_{t+2} + i_t - i_{t+1}$. Where it is the current measured at a given point in time and $i_{t-1}$ the current measured one time point earlier; $i_{t-2}$, two time points earlier; $i_{t+1}$, one time point later and $i_{t+2}$, two time points later. That is, the differences between the current at a given time point and the currents recorded one and two time points before and after it may be summed, in an exemplary embodiment.

The clot time can be defined as, according to an exemplary embodiment, the latest time-point where the transformed data exceeded a defined threshold. In this case a threshold of 1.5 was appropriate. By using this algorithm, the meter only needs to collect data for 3 seconds past the clot time, in one exemplary embodiment. It will be evident to one skilled in the art that the exact form of the transformation and the threshold level can be adjusted according the distance between the electrodes (which is related to the time constant for the transient), the density of data collection, the frequency of movement of the magnet, the concentration of electrochemical mediators, etc. Also, the "peak identifying algorithm" can be restricted to particular phases of the magnet's movement in order to further discriminate between peaks and noise, in an exemplary embodiment.

The meter, knowing when the magnetic field is varied, can determine if the electrochemical current rises above a pre-determined level within a pre-determined time, according to one exemplary embodiment. If such a peak occurs, then the particles are still mobile and the sample has not gelled.

To move the magnetic particles in the strip, the meter may vary the magnetic field. This can be done, according to an exemplary embodiment, in a number of ways. In one exemplary embodiment, a permanent magnet may be moved from one side of the strip to the other. Another exemplary approach is to have a permanent magnet on each side of the strip mounted such that as one magnet approaches the strip the other moves away. Thus, the magnetic field of each magnet may dominate in turn. In some situations, a greater response to the magnet movement can be seen if the magnets are offset from one another such that they draw the beads to slightly different lateral positions in the strip. Drawing the beads laterally helps to spread the beads over a greater area, which can enhance the signal.

An even more sensitive approach, according to another exemplary embodiment, is to use opposing permanent magnets. That is, the magnet on one side of the strip is fixed while the magnet on the other side is moved by the meter, typically parallel to the plane of the strip. The two magnets are orientated so that their poles oppose one another.

An alternative to mechanically moving permanent magnets, according to an exemplary embodiment is to use electromagnets. The electromagnets can be switched on or off with the direction of the current determining polarity, instead of being physically moved. A further option, according to another embodiment, is to use an electromagnet in combination with a permanent magnet. A range of considerations such as, e.g., but not limited to, power requirements, size, heat generation, etc., can determine if electromagnets or permanent magnets are more suitable.

Alternative Exemplary Configurations

According to an exemplary embodiment, the electrodes need not be approximately parallel and opposed; instead the electrodes in another embodiment could be, for example, side-by-side. Such co-planar electrodes typically take longer to reach a steady state current, which may be indistinguishable from zero. This is because the electroactive species above the anode is converted from the reduced to the oxidized form and vice versa for the cathode. Initially, the solution near each electrode is depleted of one species and enriched in the other. The solution further away from the electrode is less affected and diffusion causes replenishment of the depleted species at the electrode. However, eventually the electroactive species above each electrode is effectively purely reduced or oxidized. There is normally negligible lateral flow of solution from above one electrode to the other so this concentration difference remains and no more electrical current flows. The time taken to reach this state can depend, amongst other things, on the applied voltage. If a sufficiently low potential is applied then the assay could be conducted during the time taken to reach the steady state current. Movement of magnetic particles can accelerate the diffusion of the depleted electroactive species from above the electrode to the electrode surface and thus produce transient peaks in electrical current. Cessation of the peaks can indicate immobilization of the particles. However, once the electrical current reaches zero, the magnetic particle movement could not be detectable.

Alternatively, the magnetic particle movement may be used to mix solution from one electrode to the other and can induce a transient rise in current. This approach could still detect particle movement once the steady state current had been reached.

The coagulation sensor 200, according to the exemplary embodiment, has been described as having two chambers: a fill channel 201 and a detection chamber 202. The fill channel 201 can provide a convenient way to transfer the sample into the thermoregulated environment of the meter. However, the sensor 200 can be composed of a single chamber in order to reduce the volume of the analyte liquid required. This could work particularly well for assays that do not require temperature regulation or where the result can be corrected for the measured temperature. Alternatively, if temperature regulation is required, the sample could be added directly to the single reaction chamber outside the meter 300, then the strip 304 could be drawn into the meter 300 where the temperature of the reaction is controlled.

In the example of a coagulation sensor 200, in an exemplary embodiment, a device for measuring prothrombin time has been described. The specificity of the assay is determined by the coagulation reagent that is included in the strip 304. Reagents for other coagulation assays could be used instead. Such reagents may contain contact activators, snake venoms, or phospholipids.

The addition of normal coagulation factors to a sample deficient in the factors can correct the deficiency and result in a normal clot time. This technique can be used to distinguish factor deficiencies from other causes of prolonged coagulation (eg inhibitors, heparin). This technique also has application as a control reaction in INR testing because warfarin acts to induce deficiency in coagulation factors II, VII, IX, and X. Thus the clot time of a blood sample from a person on warfarin, mixed with these factors, should result in a normal clot time, while the result on the sample alone, will be longer than normal. The control reaction can demonstrate that the patient's clot time is only affected by warfarin and not, say, heparin.

The coagulation sensor can be modified to detect coagulation factor deficiencies, or to include a control reaction for INR determination. To do this, reagent containing the required clotting factors can be dried in the strip 304 along with the coagulation reagent. In some instances the clotting factors and the reagent may be able to be mixed but usually it is preferable to place them on different surfaces within the cell so that they only mix when the sample is added.

The invention claimed is:

1. A method for electrochemically monitoring the mobility of particles in a fluid in response to an external field, the method comprising:

monitoring an electrical characteristic of the fluid in an electrochemical cell, the fluid comprising particles that can be moved under the influence of the external field, wherein the particles are magnetic, wherein the external field comprises a changing external magnetic field;

observing the electrical characteristic caused by the movement of the magnetic particles induced by the external field, wherein the magnitude of the electrical characteristic can change due to a change in the mobility of the magnetic particles; and detecting a change in the mobility of the magnetic particles from a change in the magnitude of the electrical characteristic observed.

2. The method of claim 1, wherein the fluid further comprises at least one soluble electroactive species that is capable of being oxidized or reduced at an electrode in the electrochemical cell.

3. The method of claim 2, wherein the electrical characteristic being measured is the electrochemical current by amperometry.

4. The method of claim 2, wherein the electroactive species are salts of ferricyanide and ferrocyanide.

5. The method of claim 2, wherein the fluid is whole blood or plasma and the change in the physical state of the blood or plasma is due to coagulation.

6. The method of claim 5, wherein the electrical characteristic is the electrochemical current, wherein an algorithm is adapted to identify peaks in the electrochemical current that are caused by magnetic particle movement and determine the clotting time of blood or plasma.

7. The method of claim 6, wherein the algorithm defines the clot time based on when the $n^{th}$ percentile of the data around each point falls below a predetermined threshold, where the $n^{th}$ percentile is in the range of 50-$100^{th}$ percentile.

8. The method of claim 7, wherein the $n^{th}$ percentile is around the $80^{th}$ percentile.

9. The method of claim 6, wherein the algorithm calculates the height of peaks in current and defines the clot time based on when the peak height falls below a predetermined threshold.

10. The method of claim 6, wherein the algorithm makes peaks in current easier to identify by calculating $i_t-i_{t-2}+i_t-i_{t-1}+i_t-i_{t+2}+i_t-i_{t+1}$ or $i_t-i_{t-1}+i_t-i_{t+1}$, where $i_t$ is the current measured at a given point in time and $i_{t-1}$ the current measured one time point earlier; $i_{t-2}$, two time points earlier; $i_{t+1}$, one time point later and $i_{t+2}$, two time points later.

11. The method of claim 6, wherein the algorithm determines if a peak in current occurred within a predetermined time of changing the magnetic field and defines the clot time based on whether such a peak is under a predetermined threshold.

12. The method of claim 2, wherein the electrochemical cell comprises a strip comprising two electrodes.

13. The method of claim 12, wherein said two electrodes are parallel to each other and are separated by 0.05 to 0.5 mm.

14. The method of claim 12, wherein said two electrodes are parallel to each other and are separated by 0.075-0.15 mm.

15. The method of claim 12, wherein said two electrodes are parallel to each other and are separated by 0.09-0.13 mm.

16. The method of claim 12, wherein said two electrodes are coplanar.

17. The method of claim 12, wherein said two electrodes are separated by an electrically insulating layer, where the layer has a cavity cut in it to receive fluid, as well as an entry port to allow the fluid to enter the cavity and an exit port for the displaced air.

18. The method of claim 12, wherein the fluid is whole blood or plasma and a change in the physical state of the blood or plasma is due to coagulation, wherein the fluid is deficient in clotting factors, wherein said strip contains one or more clotting factors which can replace the deficient clotting factors in the fluid.

* * * * *